United States Patent [19]

Alpers et al.

[11] Patent Number: 4,990,685
[45] Date of Patent: Feb. 5, 1991

[54] PROCESS FOR THE PREPARATION OF AQUEOUS FORMALDEHYDE SOLUTIONS

[75] Inventors: Heinz-Jürgen Alpers; Karl-Heinz Dietz, both of Krefeld; Bernd-Ulrich Schenke, Bottrop; Reinhard Thiel, Krefeld, all of Fed. Rep. of Germany

[73] Assignee: Bayer Aktiengesellschaft, Leverkusen, Fed. Rep. of Germany

[21] Appl. No.: 371,786

[22] Filed: Jun. 27, 1989

[30] Foreign Application Priority Data

Jul. 19, 1988 [DE] Fed. Rep. of Germany ....... 3824360
Oct. 8, 1988 [DE] Fed. Rep. of Germany ....... 3834323

[51] Int. Cl.$^5$ ....................... C07C 45/29; C07C 45/38
[52] U.S. Cl. .................................... 568/491; 568/487; 568/493
[58] Field of Search ................ 568/472, 473, 491, 487, 568/493

[56] References Cited

U.S. PATENT DOCUMENTS

| 2,773,101 | 12/1956 | Smith et al. | 568/860 |
| 2,947,750 | 8/1950 | Cerg | 568/473 |
| 4,097,535 | 6/1978 | Yang et al. | 568/473 |
| 4,584,412 | 4/1986 | Aicher et al. | 568/473 |
| 4,594,457 | 6/1986 | Yoshikawa et al. | 568/473 |

FOREIGN PATENT DOCUMENTS 0215644 10/1985 Japan .................................... 568/491

Primary Examiner—Werren B. Lone
Attorney, Agent, or Firm—Sprung Horn Kramer & Woods

[57] ABSTRACT

In a process for the preparation of aqueous formaldehyde solutions consisting of the following steps:
(a) reaction of a methanol/water/air mixture in vapor form at elevated temperature over a catalyst,
(b) absorption of the reaction mixture in one or more successive absorption stages with the formation of a methanol-containing aqueous formaldehyde solution and
(c) removal by fractional distillation of a fraction esentially containing methanol and water, the methanol/water/air mixture which is required for the reaction is evaporated by means of heat which is withdrawn by indirect heat exchange from the formaldehyde solution being formed in the absorber and/or at least some of the vapors obtained by fractional distillation are condensed by means of liquid water. This condensate is fed together with fresh methanol and with air into the evaporator which is upstream from the catalyst stage.

12 Claims, 3 Drawing Sheets

PROCESS FOR THE PREPARATION OF AQUEOUS FORMALDEHYDE SOLUTIONS

BACKGROUND OF THE INVENTION

1. Field of the Invention

The present invention relates to a process for the preparation of aqueous formaldehyde solutions, from which most of the heat of condensation and absorption released during their preparation is withdrawn and used for evaporating the methanol/water/air mixture required. Furthermore, some of the heat content of the formaldehyde solution produced can be utilized for the recovery of methanol which is contained in the formaldehyde solution. Both measures can be used either individually or simultaneously.

Formaldehyde is an important basic chemical, for example for the preparation of phenol-formaldehyde resins or urea-formaldehyde resins, and is furthermore used as disinfectant and as tanning agent.

2. Description of the Related Art

The preparation of formaldehyde by oxidative dehydrogenation of methanol has been known for a long time. In this reaction, completely evaporated mixtures of methanol, water and air, the composition of which can vary within wide limits outside the range of explosive mixtures, are reacted over catalysts at elevated temperature. Suitable catalysts are silver catalysts and others. The gaseous mixture which leaves the catalyst stage is then converted in absorbers into aqueous formaldehyde solutions. In this reaction, a considerable portion of the heat content of the gases to be absorbed and the heat of absorption and condensation have to be removed. It is therefore desired to utilize this energy which is obtained at a low temperature level in an economic manner. The methanol/water/air mixture required for the preparation of formaldehyde solutions is usually produced in an evaporator by heating with steam.

Surprisingly, it has now been found that the complete evaporation of the methanol/water/air mixture can be carried out in a suitable evaporator below the boiling point of the methanol/water mixture and that the temperature of the aqueous formaldehyde solution formed in the absorber is sufficient for heating.

It is further desired not only to remove most of the methanol from the formaldehyde solution prepared and to reuse it, but also to remove some of the water, in order to have a more concentrated formaldehyde solution available, for example, to save transport costs. This removal of methanol and water is carried out by distillation, preferably under reduced pressure. Such a distillation under reduced pressure is advantageously carried out as flash evaporation, utilizing the heat contained in the crude formaldehyde solutions (EP 100,809). The more the pressure in such a flash evaporation is reduced, the further the column temperature drops, which corresponds to a steadily increasing and desirable utilization of energy. However, this utilization of energy has its limit in terms of economics, since at lower temperatures the condensation of the vapours is only possible by means of highly enlarged condenser surfaces and by using expensive coolants. This cancels the economic advantage of the utilization of energy and eventually turns it into a disadvantage.

Furthermore, it has now been found that the use of expensive coolants can be omitted even at very low pressures in the flash evaporation column, if the condensation of the vapours is carried out as injection condensation by means of liquid water and the resulting methanol-containing aqueous solution which has a low formaldehyde concentration and therefore has to be disposed of, is fed into the catalytic dehydrogenation of methanol instead of the water, which is required as a starting material.

The possibility of operating at very low column pressures also makes it possible to carry out both measures simultaneously and thus achieve optimum utilization of the heat contained in the formaldehyde solution.

The advantages of such a procedure are as follows:
1. saving of the steam required for the evaporation of the methanol/water/air mixture;
2. saving of methanol while utilizing most of the energy, in particular in the lower pressure range of the flash evaporation so that the process can be managed without external energy;
3. the possibility of also using methanol/water mixtures of lower concentrations and
4. the possibility of doing without a too high methanol conversion.

The measures mentioned in 3. and 4. promote the selectivity of the catalytic dehydrogenation and thus the yield and are only possible because an extensive recovery of methanol is possible according to the invention in an economic manner.

SUMMARY OF THE INVENTION

The invention accordingly relates to a process for the preparation of aqueous formaldehyde solutions consisting of the steps
(a) reaction of a methanol/water/air mixture at elevated temperature over a catalyst,
(b) absorption of the reaction mixture in one or more successive absorbers with the formation of a methanol-containing aqueous formaldehyde solution and, if desired,
(c) removal by fractional distillation of a fraction essentially containing methanol and water from this formaldehyde solution,
which is characterized in that the methanol/water mixture required for the reaction is evaporated by indirect heating by means of a formaldehyde solution removed from the absorber or in that at least some of the vapours obtained by fractional distillation are condensed by means of liquid water and this condensate is fed together with fresh methanol and with air into the evaporator which is upstream from the catalyst stage.

BRIEF DESCRIPTION OF THE DRAWINGS

The accompanying

DETAILED DESCRIPTION OF THE INVENTION

Figure 1:
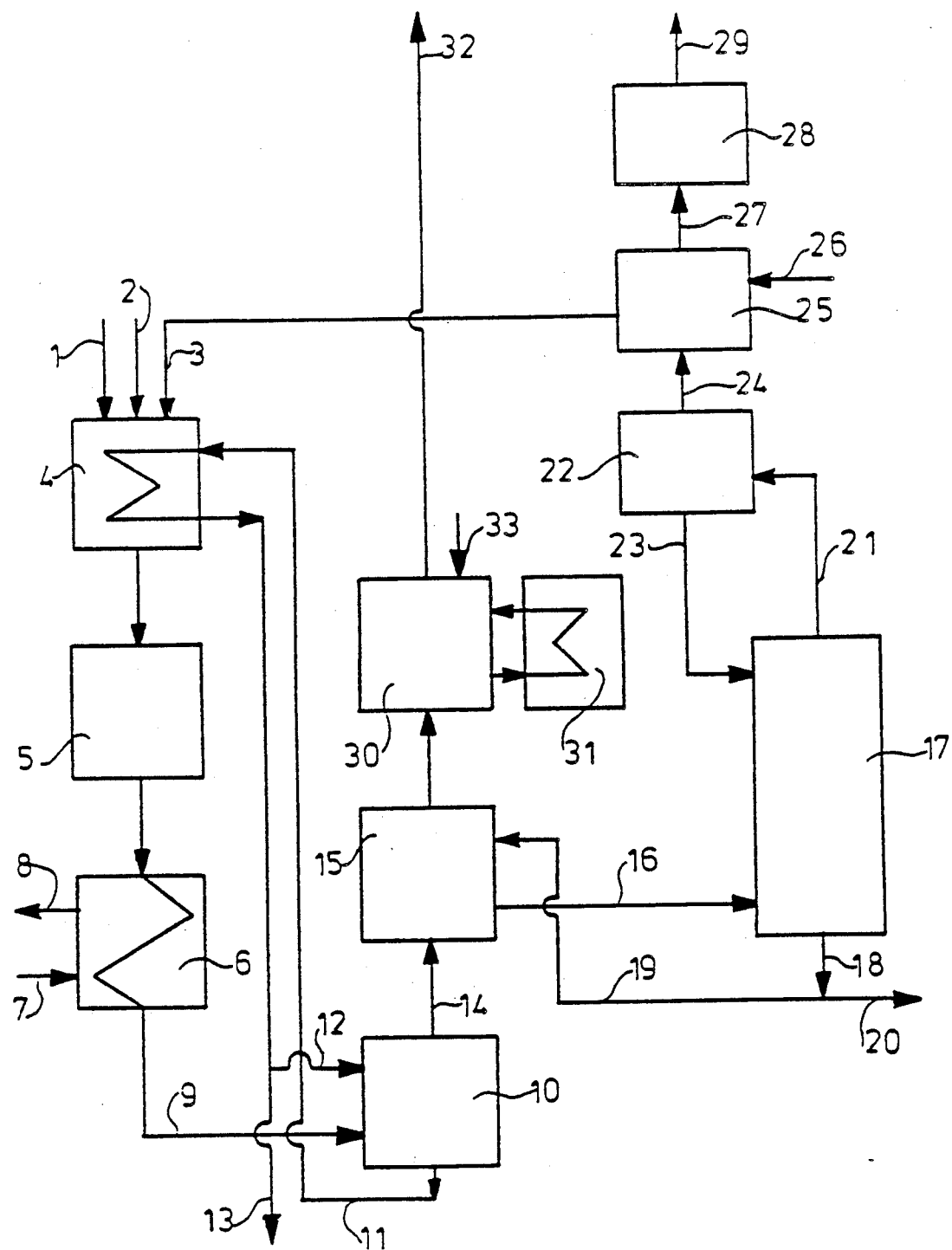
FIGS. 1, 2 and 3 show the process according to the invention, using the example of a three-staged absorption.

In a preferred variant of the process according to the invention, both characterizing measures are carried out together.

In a further preferred variant, the absorption in the process according to the invention is carried out in at least two successive absorption stages. In this case, the methanol-containing aqueous formaldehyde solution used for the fractional distillation is removed from the second absorption stage or one of the further successive absorption stages; the formaldehyde solution which is required for heating the evaporator which is upstream from the catalyst stage is removed from the first absorption stage or one of the upstream absorption stages, preferably from the first absorption stage. The formaldehyde solution which returns from the evaporator can either be removed as a product for further use or recycled into the absorption stage from which it was removed. The indirect heating by means of the formaldehyde solution removed from the absorber covers the entire or at least predominant energy demand of the evaporator. Moreover, additional heating for starting the process has been installed.

Irrespective of the wording used here of one absorber per absorption stage, it goes without saying that each absorption stage can also consist of several absorbers.

A suitable evaporator is designed such that an intensive distribution which is uniform throughout its cross-section of the components methanol/water and air is guaranteed. An evaporator of such a design can be heated without external energy, that is to say, solely by means of the formaldehyde solution removed from the absorber; the heat of absorption and condensation released in the absorption stage can largely be utilized.

The removal by fractional distillation of, for the most part, methanol and water (apart from small amounts of formaldehyde) can be carried out at a pressure of 40 to 800 mbar, measured at the column head. This pressure is preferably 50 to 44 mbar, particularly preferably 50 to 200 mbar, and very particularly preferably 50 to 95 mbar, all measured at the column head.

The vapours obtained by fractional distillation are condensed only partially on a surface condenser, in order to maintain reflux for the distillation column to the extent desired. The largest portion of the methanol leaves this surface condenser still in vapour form and is completely precipitated in a downstream injection condenser by means of added water. The resulting condensate is fed into the evaporator which is upstream from the catalyst stage. Therefore, the amount of water used for the injection condensation may preferably be as much as the total amount of water required in the methanol/water/air mixture.

Although a noticeable heat which is contained in the absorption solutions is fed into other heat-consuming stages of the process according to the invention (evaporator and/or fractional distillation) in the manner described, so that those can be operated without external energy, it is nevertheless possible to feed the gases which leave the catalyst stage into a waste heat boiler known per se without any shortage of energy occurring at the other stages described. A further preferred variant is therefore to generate the steam also in the process according to the invention in such a waste heat boiler.

With reference to the accompanying FIG. 1, the process according to the invention will be described as follows, using the example of a three-staged absorption, in which in a preferred manner the evaporator is heated by the formaldehyde solution removed from the absorber and the vapours of the flash evaporation are deposited by means of fresh water and in addition a waste heat boiler is operated:

Fresh methanol (1), air (2) and a recycled mixture (3) essentially consisting of methanol and water are completely evaporated in evaporator (4) and fed into the catalyst stage (5). The reaction mixture which leaves the catalyst stage (5) is fed into a waste heat boiler (6), where it is cooled to about 120 °C. and optionally preheated water (7) is at the same time converted into steam of 5 to 6 bar (8). The reaction mixture which leaves the waste heat boiler is fed into a first absorber stage (10) via line (9). The aqueous formalin solution formed in (10) is fed into the evaporator (4) for the purpose of heat-exchange via line (11) and some of it is recycled into the first absorber stage (10) via line (12). Some of the aqueous formalin solution from (10) is removed after the heat-exchange (4) as product stream (13). The reaction gases which were not condensed in (10) are fed into the second absorber stage (15) via line (14). The methanol-containing aqueous formaldehyde solution which leaves (15) is fed into the rectification column (17) via line (16), where flash evaporation takes place under reduced pressure. The remaining aqueous formaldehyde solution which is low in methanol is removed at the bottom of (17) via line (18) and some of it is fed as reflux into the second absorber stage (15) via line (19) and some of it is removed as product via line (20). The vapours formed in (17), which consist mainly of methanol and water in addition to small amounts of formaldehyde, are fed into a surface condenser (22) via line (21), where they are only partially condensed so as to be fed as reflux into column (17) via line (23). A portion of the vapours remains in gaseous form and is fed into an injection condenser (25) via line (24), in which all condensable portions of the vapours are deposited by means of water fed in via line (26). The condensate is fed into evaporator (4) via line (3). The uncondensable portions and the inert gas components are fed via line (27) into the vacuum pump (28), at the pressure side of which they are discharged as waste gas (29) and are transferred to a suitable disposal unit. The portion of the reaction gases which was not absorbed in the second absorber stage (15) is absorbed in a third absorber stage (30). The heat of condensation which is additionally absorbed by this absorbate is removed by means of a cooler (31). The water which is required as absorption medium is provided via (33). The uncondensable components and the inert gases are fed as waste gas (32) into a suitable disposal unit, usually a combustion unit with generation of steam.

Figure 2:
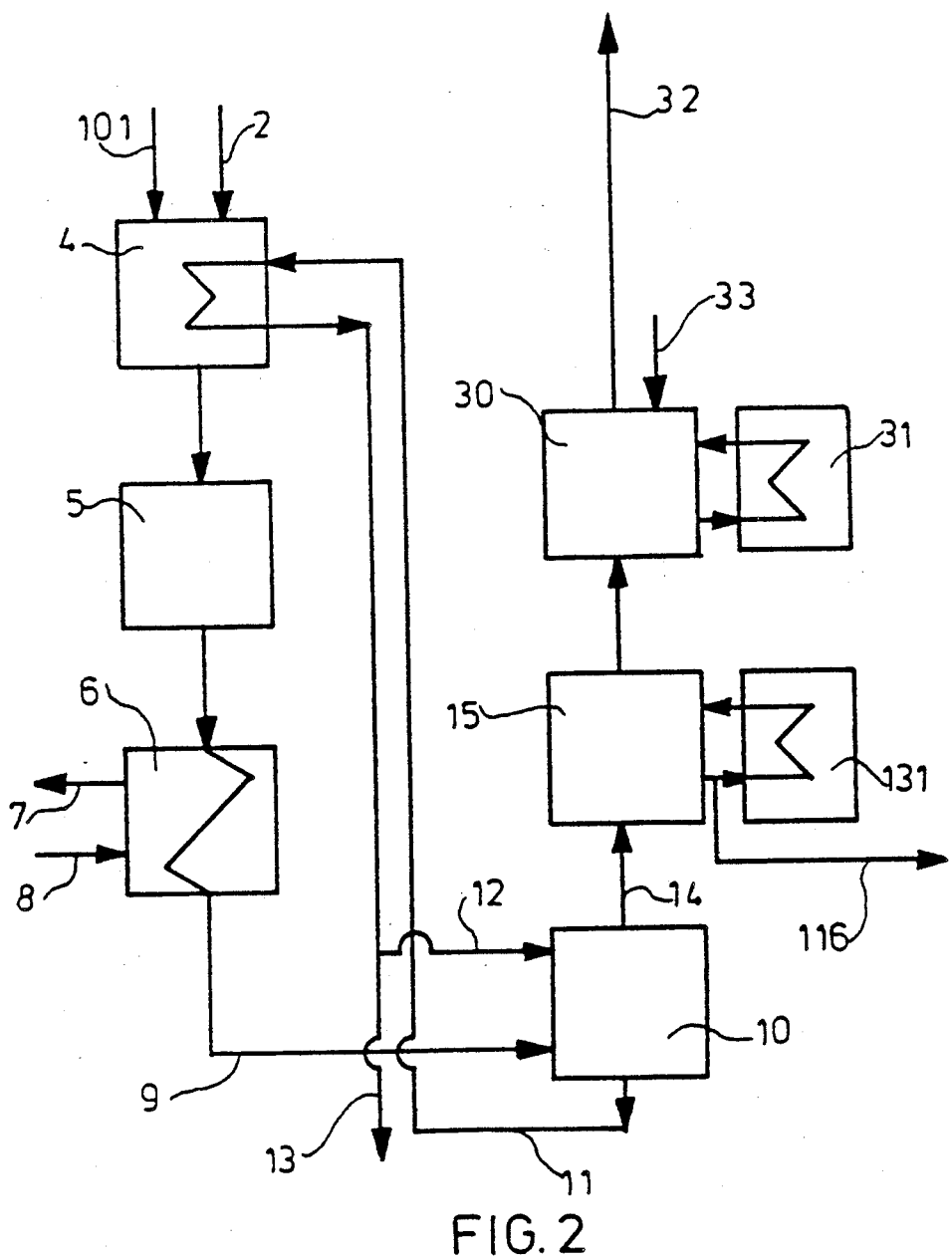

FIG. 2 shows the process according to the invention of the heating of the evaporator by means of formaldehyde solution removed from the absorber without the condensation according to the invention of the vapours in flash evaporation. Identical reference symbols have the same meanings as in FIG. 1. In addition, (101) denotes the feeding of methanol and water as a mixture, (116) a discharge line for formaldehyde solution as a product and (131) a cooler which is operated analogously to cooler (31).

Figure 3:
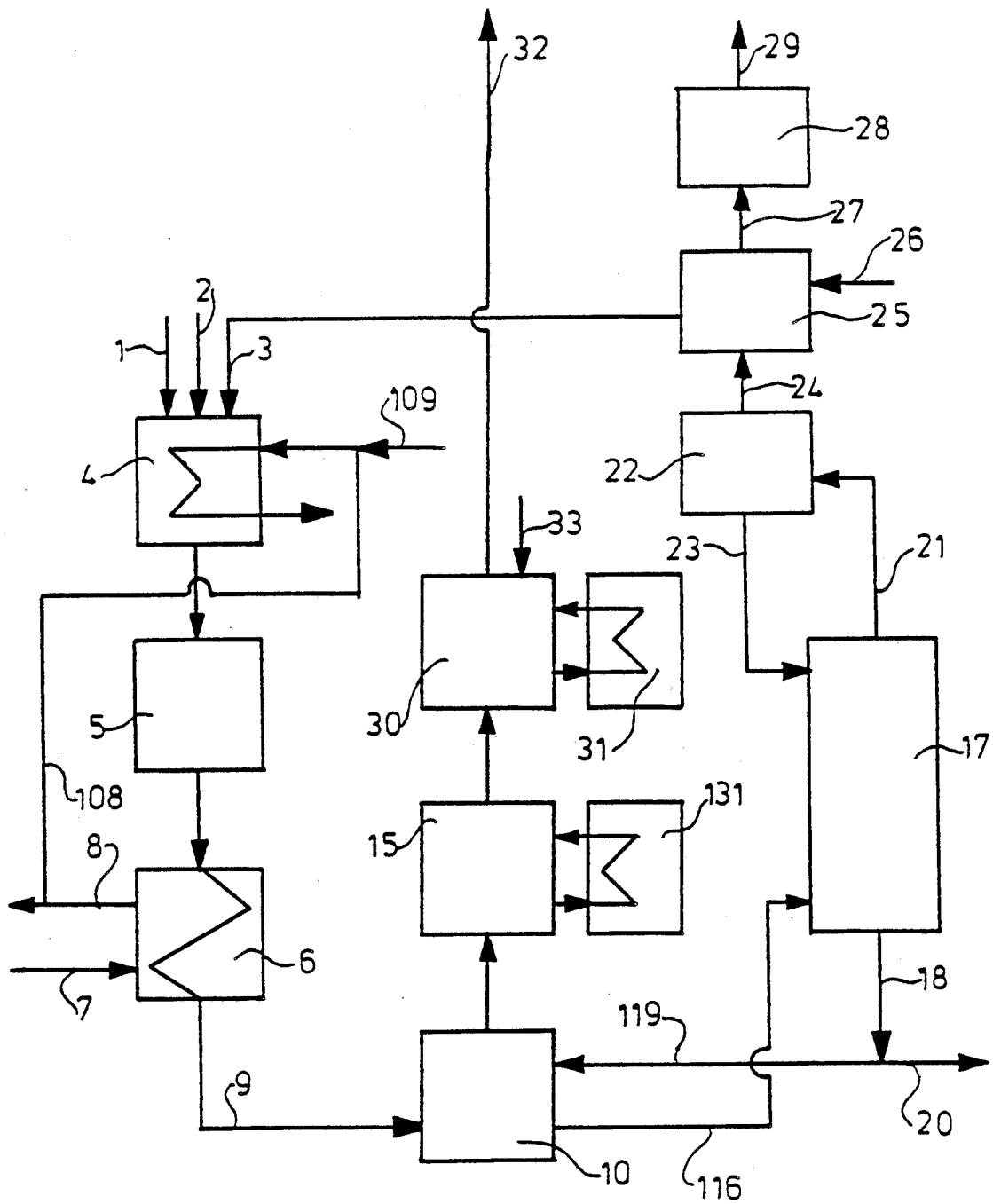

FIG. 3 shows the process according to the invention of the condensation of the vapours of the flash distillation and the feeding of the resulting condensate to the evaporator stage without the heating according to the invention of this evaporator stage. Evaporation is in this case effected by means of steam which is generated in waste heat boiler (6), supplemented by steam which is removed from the general network. Again, identical reference symbols have the same meanings as in FIG. 1. In addition, (108) denotes the line for heating steam from (6) to (4) and (109) the line for the steam to be used from the network, furthermore (116) denotes the feedline for formaldehyde solution from the first absorption stage into the rectification column and (119) the recycling of the bottom stream of (17) after the removal of the product via (20).

EXAMPLE 1

In a plant according to accompanying FIG. 2, to which the reference symbols used refer, 1,070 parts by weight of a mixture consisting of 600 parts by weight of methanol and 470 parts by weight of water together with 970 parts by weight of air are fed per hour into evaporator (4) and completely evaporated there. The gas mixture is reacted in reactor (5), which is equipped with a silver catalyst. About 630 parts by weight of steam of 5 bar are generated per hour in waste heat boiler (6) and fed into the steam network via line (8). This cools the reaction gases to about 120 °C. About 25,000 parts by weight of formaldehyde solution at 79°-83 °C. circulate from the first absorption stage (10) via line (11) to evaporator (4) and are cooled down to 68°-70 ° C. upon passing through evaporator (4). Of these, 570 parts by weight (40.5% of formaldehyde and about 1.0% of methanol) are removed per hour via line (13). In the other absorption stages (15, 30), the remaining formaldehyde and unconverted methanol are absorbed and discharged in the form of an approximately 30% strength formaldehyde solution containing about 2.2% of methanol (900 parts by weight/h) via line (116). The yield of formaldehyde, relative to the methanol used, is 89% of the theoretical yield.

EXAMPLE 2

In a plant according to FIG. 3, 583 parts by weight of methanol/h, 970 parts by weight of air/h and 480 parts by weight of condensate/h, consisting of 17 parts by weight of methanol, 460 parts by weight of water and traces of formaldehyde, are completely evaporated per hour in evaporator (4) and fed into reactor (5), which is equipped with a silver catalyst. About 630 parts by weight of steam of 5 bar are generated per hour in waste heat boiler (6) and fed into evaporator (4) together with about 180 parts by weight of fresh steam via lines (108) and (109). The reaction gases are cooled to about 120 °C. in the waste heat boiler. From the first absorption stage (10), about 27,000 parts by weight of aqueous formaldehyde solutions circulate via line (116) to distillation column (17), 1,450 parts by weight of which are removed per hour after flash evaporation at 95 mbar of column head pressure via line (20) (34.4% of formaldehyde and 0.7% of methanol). The main stream flows back into absorber (10) via line (119). The vapours flowing through surface condenser (22) are deposited in injection condenser (25) by means of 450 parts by weight of water/h (via line 26) and give a condensate of the abovementioned composition which flows back to evaporator (4). In this procedure, the yield of formaldehyde, relative to the methanol used, is 91.3% of the theoretical yield.

EXAMPLE 3

In a plant according to FIG. 1, 583 parts by weight of methanol, 970 parts by weight of air and 480 parts by weight of condensate, consisting of 17 parts by weight of methanol, 460 parts by weight of water and residual amounts of formaldehyde, are completely evaporated per hour in evaporator (4) and fed into reactor (5), which is equipped with a silver catalyst. About 630 parts by weight of steam of 5 bar are generated per hour in waste heat boiler (6) and fed into the general steam network via line (8). This cools the reaction gases to about 120° C. From the first absorption stage, about 25,000 parts by weight/h of aqueous formalin solution at 79°-83 °C. circulate via line (11) to evaporator (4) and are cooled down to 68°-70° C. upon passaging through evaporator (4). Of these, 570 parts by weight of aqueous formaldehyde solution (40.5% of formaldehyde and about 1% of methanol) are removed per hour via line (13). From the second absorption stage (15), about 27,000 parts by weight of aqueous formaldehyde solution circulate to the rectification/ flash evaporation column (17), 880 parts by weight of which are removed per hour after flash evaporation at 85 mbar of column head pressure via (20) (30.5% of formaldehyde and 0.5% of methanol). The vapours which pass through the surface condenser (22) are deposited in injection condenser (25) by means of 450 parts by weight of water/h (via (26)) and give a condensate of the abovementioned composition which flows back to evaporator (4). The yield of formaldehyde, relative to the methanol used, is 91.3% of the theoretical yield.

What is claimed is:

1. A process for the preparation of aqueous formaldehyde solutions comprising the steps of
    (a) reaction of a methanol/water/air mixture in vapor form at an elevated temperature over a catalyst and
    (b) absorption of the reaction mixture from (a) in one or more successive absorption stages, with the formation of a methanol-containing aqueous formaldehyde solution, wherein the methanol/water mixture required for the reaction is evaporated by indirect heating by means of a formaldehyde solution removed from the absorption stages.

2. A process for the preparation of aqueous formaldehyde solutions comprising the steps of
    (a) reaction of a methanol/water/air mixture at an elevated temperature over a catalyst in a catalyst stage,
    (b) absorption of the reaction mixture from (a) in one or more successive absorption stages with the formation of a methanol-containing aqueous formaldehyde solution and
    (c) removal by fractional distillation of a fraction essentially containing methanol and water, wherein at least some of the vapors obtained by the fractional distillation are condensed by means of liquid water to form a condensate and said condensate is fed together with fresh methanol and with air into an evaporator, which is upstream from the catalyst stage.

3. The process for the preparation of aqueous formaldehyde solutions according to claim 2, comprising the steps of
    (a) reaction of a methanol/water/air mixture in vapor form at an elevated temperature over a catalyst,
    (b) absorption of the reaction mixture from (a) in one or more successive absorption stages with the formation of a methanol-containing aqueous formaldehyde solution and
    (c) removal by fractional distillation of a fraction essentially containing methanol and water, wherein the methanol/water mixture required for the reaction is evaporated in an evaporator by indirect heating by means of a formaldehyde solution removed from the absorption stages and at least some of the vapors obtained by the fractional distillation are condensed by means of liquid water to form a condensate and said condensate is fed together with fresh methanol and with air into the evaporator, which is upstream from the catalyst stage.

4. The process according to claim 3, wherein the absorption is carried out in at least two successive absorption stages and the formaldehyde solution removed from a first absorption stage is fed into the evaporator for the purpose of heat-exchange and wherein the methanol-containing aqueous formaldehyde solution which is used for the fractional distillation is removed from a downstream absorption stage.

5. The process according to claim 2, wherein the fractional distillation is carried out at a pressure of 40 to 800 mbar, measured at the column head.

6. The process according to claim 5, wherein the fractional distillation is carried out at a pressure of 50 to 400 mbar, measured at the column head.

7. The process according to claim 6, wherein that the fractional distillation is carried out at a pressure of 50 to 200 mbar, measured at the column head.

8. The process according to claim 7, wherein that the fractional distillation is carried out at a pressure of 50 to 95 mbar, measured at the column head.

9. The process according to claim 1, wherein that the mixture which leaves the catalyst stage is fed into a waste heat boiler before the absorption.

10. The process according to claim 2, wherein the mixture which leaves the catalyst stage is fed into a waste heat boiler before the absorption.

11. The process according to claim 4, wherein the downstream absorption step is a second absorption step.

12. The process according to claim 1, wherein the catalyst is a silver catalyst.

* * * * *